United States Patent

Chang et al.

[11] Patent Number: 5,852,243
[45] Date of Patent: Dec. 22, 1998

[54] METHOD AND APPARATUS FOR DETECTING A ROAD PAVEMENT SURFACE CONDITION

[75] Inventors: James Shih-Tsih Chang; James Jay Fanning, both of Colorado Springs, Colo.

[73] Assignee: J-Squared, LLC

[21] Appl. No.: 896,865

[22] Filed: Jul. 21, 1997

[51] Int. Cl.[6] .................................................. G01N 19/02
[52] U.S. Cl. .............................. 73/659; 701/80; 340/580; 340/582; 340/905
[58] Field of Search ............................. 73/590, 594, 587, 73/593, 645, 648, 649, 659, 660, 105; 180/167, 168, 169; 340/901, 905, 580, 581, 582, 583, 601, 602; 364/550, 551.01; 701/80, 1

[56] References Cited

U.S. PATENT DOCUMENTS

| | | | |
|---|---|---|---|
| 3,891,979 | 6/1975 | Braun et al. | 340/581 |
| 4,222,044 | 9/1980 | Boschung | 340/581 |
| 4,274,091 | 6/1981 | Decker | 340/583 |
| 4,335,613 | 6/1982 | Luukkala | 73/599 |
| 4,406,165 | 9/1983 | Coussineux | 73/488 |
| 4,745,803 | 5/1988 | Haavasoja | 324/699 |
| 5,521,594 | 5/1996 | Fukushima | 340/901 |
| 5,586,028 | 12/1996 | Sekine et al. | 364/423.098 |

OTHER PUBLICATIONS

"Surfing the Wavelets", http//:www.monash.edu.au/cmcm/wavelet/wavelet.htm.
"An Introduction to Wavelets", http//:www.amara.com/IEEEwave/IEEEwavelet.com.
Advertisement for "SCAN FP 2000 Sensor".
"Ice Detection and Cooperative Curve Warning", http:www-w.volpe.gov, pp. 1–15, Oct. 24, 1996.

Primary Examiner—Hezron Williams
Assistant Examiner—Rose M. Miller
Attorney, Agent, or Firm—Dale B. Halling

[57] ABSTRACT

An apparatus for determining a road pavement surface condition over a wide area has a road noise sensor (12). A temporal frequency analyzer (18) converts a road noise signal from the road noise sensor (12) to a temporal frequency signal. A processing circuit (20) receives the temporal frequency signal from the temporal frequency analyzer (18) and analyzes the temporal frequency signal to determine the road pavement surface condition.

20 Claims, 3 Drawing Sheets

METHOD AND APPARATUS FOR DETECTING A ROAD PAVEMENT SURFACE CONDITION

FIELD OF THE INVENTION

The present invention relates generally to the field of road sensors and more particularly to a method and apparatus for detecting a road pavement surface condition.

BACKGROUND OF THE INVENTION

"Black ice" on roadways can be a source of serious accidents. Black ice is dangerous because drivers can suddenly and without warning find themselves having no traction and end up losing control of the vehicle. Road pavement sensors have been developed to detect ice formation on the roadway in order to warn drivers of icy conditions. These sensors are embedded in the pavement and monitor temperature, moisture, salinity, dew point, and etc. to determine if the conditions are likely to result in ice formation. Unfortunately, these sensors are expensive and could only monitor pavement conditions at a point in the pavement. The sensors can only monitor very localized conditions and therefore cannot detect ice formation occurring a short distance from the sensors.

Thus there exists a need for a method and apparatus that can accurately and inexpensively determine ice formation over a wide area of road pavement.

SUMMARY OF THE INVENTION

A method that overcomes these and other problems of detecting a road pavement surface condition includes the steps of detecting a road noise created by a vehicle traveling along a road. Next, a temporal frequency content of the road noise is determined. Then the temporal frequency content is analyzed to determine the road pavement surface condition.

DETAILED DESCRIPTION OF THE DRAWINGS

Figure 1:
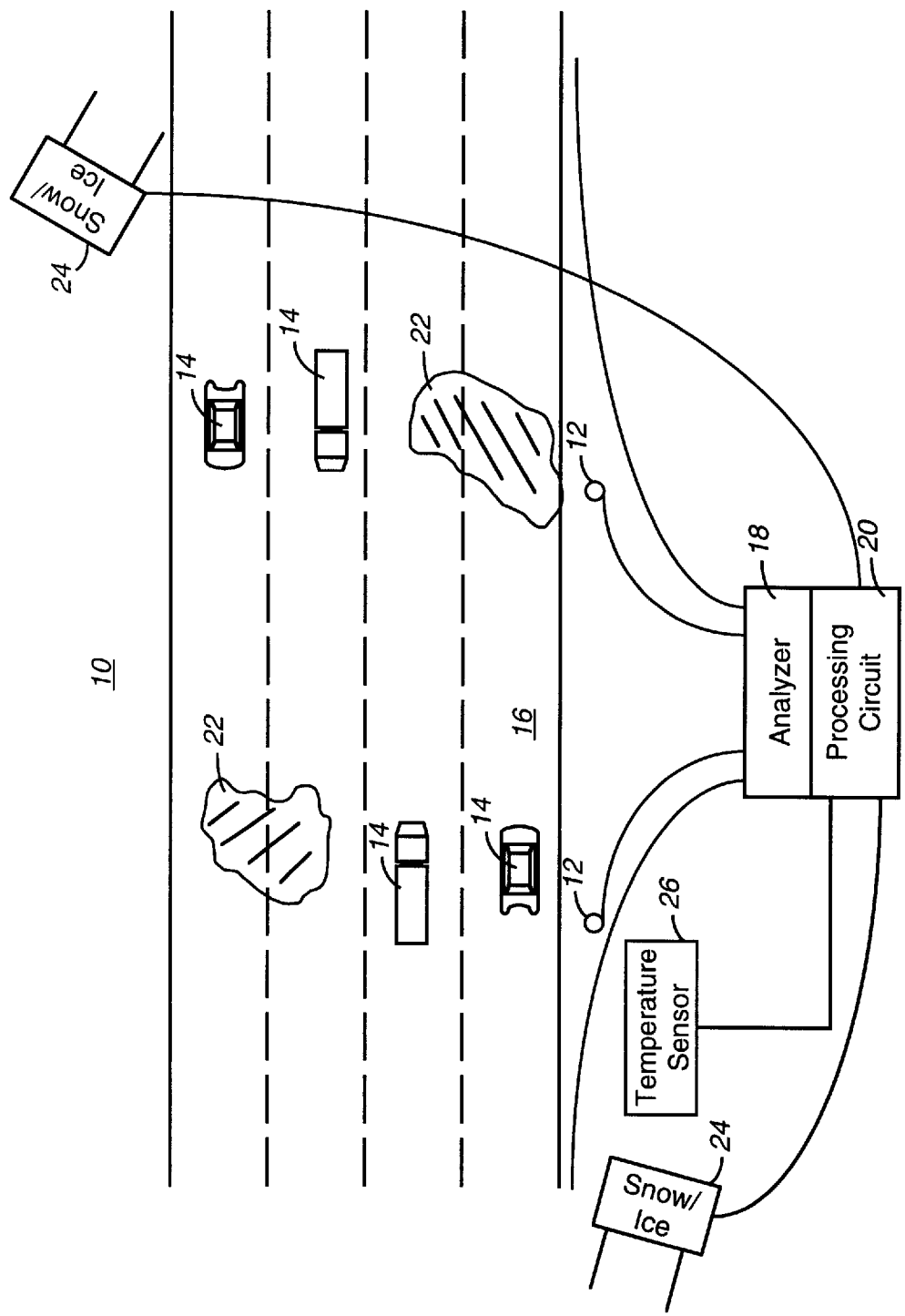
FIG. 1 is a schematic drawing of an apparatus for determining a road pavement surface condition.

A system 10 for determining a road pavement surface condition over a wide area is shown in FIG. 1. A plurality of road noise sensors 12 detect the road noise created by a vehicle's 14 tire impacting a road pavement surface 16 as the vehicle travels over the road. A temporal frequency analyzer 18 converts the road noise signal (detected signal) from the road noise sensors 12 to a temporal frequency signal. A processing circuit (e.g., microprocessor) 20 analyzes the temporal frequency signal to determine the road pavement surface condition around each of the road noise sensors 12. When the processor 20 determines that the road pavement surface contains a patch of snow or ice 22, it has a communication output port over which it sends a road condition message. In one embodiment the communication output port activates an electronic sign 24 warning drivers of the condition. In other embodiments, the communication output port is connected to a modem and transmits the road condition over a phone line, radio link or other communication medium to a receiver requiring the road condition information.

In one embodiment a temperature sensor 26 is located near each road noise sensor (sound energy detection sensor) 12. The temperature sensor 26 sends a temperature signal to the processing circuit 20. The processing circuit 20 uses the temperature sensor 26 to determine a temperature trend. When the temperature is near freezing (e.g., 32° Fahrenheit or 0° Centigrade) the temperature trend is used in conjunction with road noise measurements and analysis to determine if ice is about to form (ice forming state). In that case the processor 20 can send a signal to the sign 24 to display "ice forming." In another embodiment, the sign tells motorist that the pavement is wet/slushy.

In another embodiment the road noise sensor 12 is mounted on a moving vehicle 14. In yet another embodiment, the moving vehicle 14 also contains the analyzer 18, the processing circuit 20 and the temperature sensor 26. This allow the vehicle 14 to determine the state of the road autonomously. Road maintenance vehicles laying salt (sand, other) can use the system to determine the areas that require more salt or no salt.

The basic principle used in determining the state of the road is that the frequency of the road noise changes if the road condition is wet/slushy or dry or snow/ice packed. A temporal frequency signal of the road noise is determined. The temporal frequency signal can be determined using wavelet analysis or short time Fourier transforms or any of a number of other temporal frequency analysis tool. Note that even a standard Fast Fourier Transform (FFT) can provides crude temporal frequency information and can be used for this application. When the road is dry the road noise will be relatively uniformly spread over a road noise frequency band (in one embodiment the noise frequency band is 1 KHz to 20 KHz) and essential constant in time. When the road is wet/slushy the road noise will be accentuated in the higher frequencies of the road noise frequency band and can vary in time. Time variations can result from puddles and dry spots. The time variations can be used to locate the position of puddles, dry spots or other discontinuities. When the road is snow/ice packed the road noise will be accentuated in the lower frequencies of the road noise frequency band and can vary in time. Again the variations indicate dry, wet or snow patches.

The processor 20, in one embodiment stores a sensed dry state road condition and compares it with the input road noise. When the temporal frequency content deviates from the dry road pavement surface condition temporal frequency data in a predetermined manner, determining a snow/ice condition exists. For instance, when the low frequency energy content increases (or the high frequency content is attenuated), the processor determines that the road condition is icy or snow packed.

The processor 20 is only concerned with the road noise due to the impact between the tire and the road surface. As a result, low frequencies related to engine noise created by the vehicle are therefore of no value in determining the state of the road. Engine and other intrinsic vehicle noises and other non-road-noise components in this temporal frequency range are removed before the processor analyzes the temporal frequency signal to determine the state of the road.

The system 10 can determine the road pavement surface condition over a wide area of the road, including multiple lanes of traffic, because the road noise sensor can detect noise over an extend distance.

Figure 2:
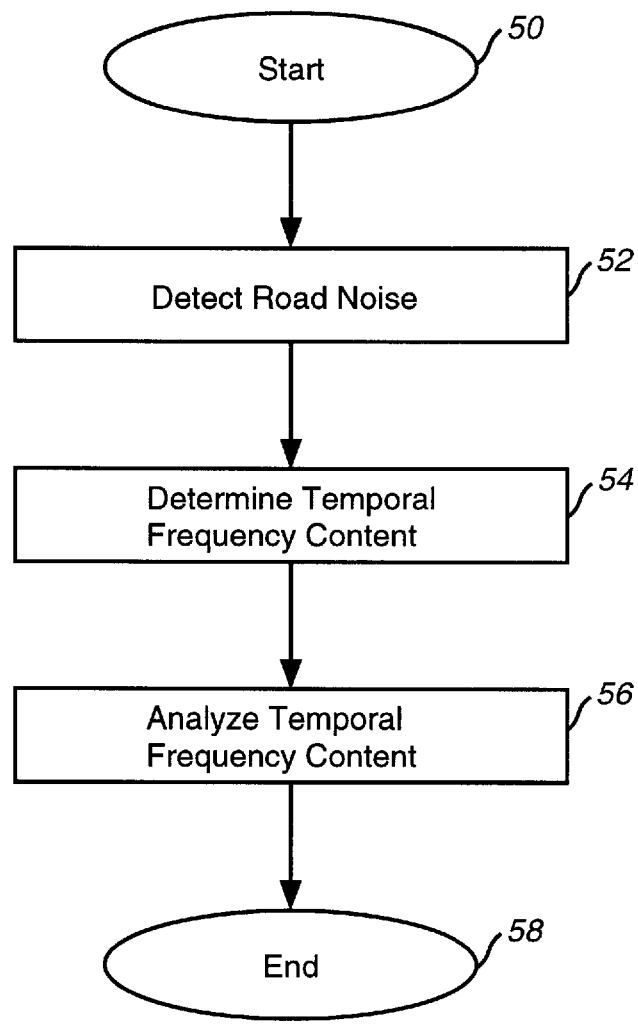
FIG. 2 is a flow chart of an embodiment of the steps taken to determine a road pavement surface condition.

FIG. 2 is a flow chart of an embodiment of the steps taken to determine a road pavement surface condition. The process starts, step 50, by detecting a road noise created by a vehicle traveling along a road at step 52. The road noise can be detected by a microphone, transducer or other detector capable of detecting pressure variations caused by a sound wave. The road noise sound wave can be detected through the air, through the ground (pavement or road shoulder) or through a road structure, such as a beam of a bridge to which it is attached. The temporal frequency content of the road noise is then determined at step 54. In one embodiment the temporal frequency content is determined by filtering the road noise into at least two frequency bands and detecting the energy (energy content) in the frequency bands. This is done by a filter bank having a filter (at least one frequency filter). In another embodiment the detected road noise is digitized. A temporal frequency transform of the digitized signal is then performed to obtain the temporal frequency content. The temporal frequency transform can be accomplished using a short time Fourier transform, wavelet analysis or other temporal frequency transforms. Next the temporal frequency content is analyzed at step 56, which ends the process at step 58. In one embodiment, the energy content in the at least two temporal frequency brands are compared. When the ratio of the energy contents is within a predetermined range, determining a snow/ice road condition exists. In another embodiment a dry road pavement surface condition temporal frequency data is stored. Then input samples of temporal frequency data are compared to the dry temporal frequency data. When the upper half of the spectrum starts to attenuate and/or the lower half of the spectrum is amplified, a snow/ice road condition exists.

Figure 3:
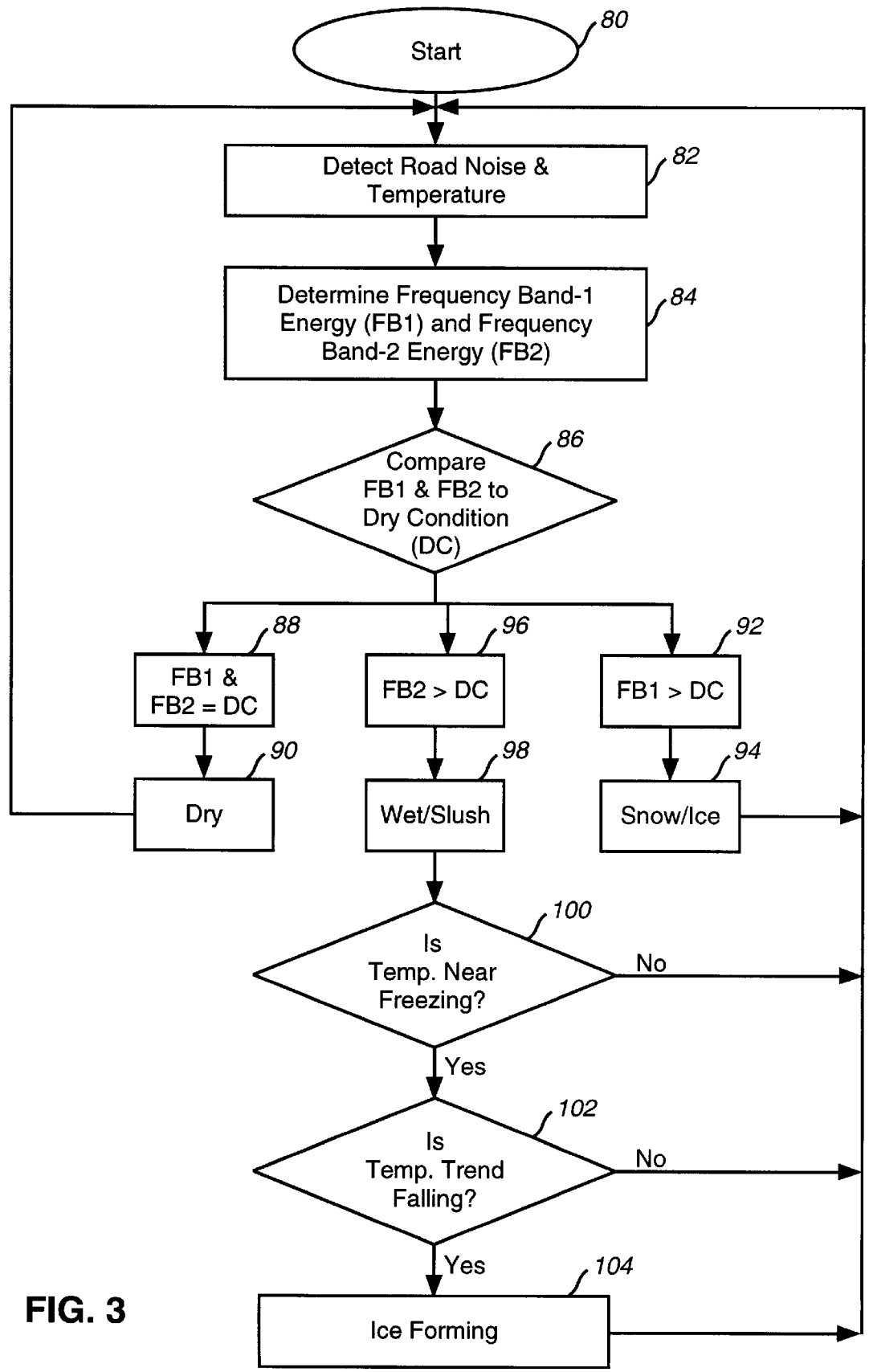
FIG. 3 is a flow chart of an embodiment of the steps taken to determine a road pavement surface condition.

FIG. 3 shows a flow chart of another embodiment of the steps used in determining a state of the road. The process starts, step 80, by detecting an energy emission from a tire impact the road and by detecting the temperature near the road at step 82. Next, the detected signal is converted into two frequency bands and the energy of the two frequency bands is determined at step 84. The exact frequencies at which the two frequency bands are divided, depend on a number of factors, including the type of road surface, wear of the road and others. The exact dividing frequencies can be determined by observation of the temporal frequency data for a road under different road conditions. Next, the energy of the two frequency bands are compared to a dry road condition temporal spectral content at step 86. When the energy or the two bands are approximate equal to the dry road condition (dry state road noise temporal spectral content) at step 88, then it is determined that the road condition is dry at step 90. When the energy or the lower frequency band (frequency band one) of the two frequency bands is greater than the dry road condition by a predetermined amount at step 92, then it is determined that a snow/ice road condition exists at step 94. When the higher frequency band (frequency band 2) of the two frequency bands is greater than the dry condition by a predetermined amount at step 96, then it is determined that a wet/slush road condition exists at step 98. At step 100 it is determined if the temperature is near freezing. When the temperature is not near freezing, then processing continues at step 82. When the temperature is near freezing, it is determined if the temperature trend is falling at step 102. When the temperature trend is not falling, then processing continues at step 82. When the temperature trend is falling, then it is determined that ice is forming at step 104. While the device has been described in conjunction with determining if a road is wet, dry or icy many other applications will be apparent to those skilled in the art. For instance, oil spills and sand patches are detectable.

Using the method and apparatus described above the state of a road can be inexpensively determined over a wide area of the road. While the invention has been described in conjunction with specific embodiments thereof, it is evident that many alterations, modifications, and variations will be apparent to those skilled in the art in light of the foregoing description. Accordingly, it is intended to embrace all such alterations, modifications, and variations in the appended claims.

What is claimed is:

1. A method of detecting a road pavement surface condition comprising the steps of:
    (a) detecting a road noise created by a vehicle traveling along a road;
    (b) determining a temporal frequency content of the road noise; and
    (c) analyzing the temporal frequency content to determine the road pavement surface condition.

2. The method of claim 1, wherein step (a) further includes the steps of:
    (a1) receiving the road noise at a sound energy detection sensor;
    (a2) digitizing the road noise.

3. The method of claim 1, wherein step (b) further includes the step of performing a temporal frequency transform of the road noise.

4. The method of claim 1, wherein step (b) further includes the steps of:
    (b1) filtering the road noise into at least two frequency bands;
    (b2) detecting an energy for the at least two frequency bands.

5. The method of claim 4, wherein step (c) further includes the steps of:
    (c1) comparing an energy content of the at least frequency bands;
    (c2) when a ratio of the energy content of the at least two frequency bands is within a predetermined range, determining that a road condition exists.

6. The method of claim 1, wherein step (c) further includes the steps of:
    (c1) storing a dry road pavement surface condition temporal frequency data;
    (c2) comparing the temporal frequency content to the dry road pavement surface condition temporal frequency data.

7. The method of claim 6, further including the steps of:
    (c3) when the temporal frequency content deviates from the dry road pavement surface condition temporal frequency data in a predetermined manner, determining that a condition exists other than a dry road pavement surface condition.

8. The method of claim 1, further including the step of:
    (d) sensing a temperature near the road.

9. The method of claim 8, further including the step of:
    (e) determining a temperature trend;
    (f) analyzing the temperature trend and the road noise to predict if the road pavement surface condition is about to change.

10. An apparatus of determining a road pavement surface condition, comprising:
    a road noise sensor;
    a temporal frequency analyzer converting a road noise signal from the road noise sensor to a temporal frequency signal; and
    a processing circuit receiving the temporal frequency signal from the temporal frequency analyzer and analyzing the temporal frequency signal to determine the road pavement surface condition.

11. The apparatus of claim 10, further including a temperature sensor, the temperature sensor sending a temperature signal to the processing circuit.

12. The apparatus of claim 11, wherein the processing circuit determines a temperature trend from the temperature signal.

13. The apparatus of claim 10, wherein the temporal frequency analyzer includes at least one frequency filter.

14. The apparatus of claim 10, wherein the processing circuit is a microprocessor.

15. The apparatus of claim 10, further including a communication output coupled to the processing circuit.

16. The apparatus of claim 10, wherein the road noise sensor is located at a fixed point relative to a road structure.

17. A method for determining a state of a road pavement, comprising the steps of:
   (a) detecting, with a road noise sensor mounted on a moving vehicle, an energy emission from a tire impacting the road to form a detected signal;
   (b) converting the detected signal into a temporal spectral content; and
   (c) analyzing the temporal spectral content to determine the state of the road pavement.

18. The method of claim 17, wherein step (a) further includes the step of:
   (a1) detecting, with a temperature sensor on the moving vehicle, a temperature near the road pavement;
   (a2) determining a temperature trend.

19. The method of claim 18, wherein step (c) further includes the step of:
   (c1) analyzing the temperature trend and the temporal spectral content to determine the state of the road pavement.

20. The method of claim 19, wherein step (c1) further includes the step of:
   (i) storing a dry state road noise temporal spectral content;
   (ii) monitoring the temperature trend;
   (iii) when the temporal spectral content deviates from the dry state road noise temporal spectral content in a predetermined manner and when the temperature trend is falling, determining that an ice forming state exists.

* * * * *